United States Patent [19]

Fisher et al.

[11] Patent Number: 4,813,422
[45] Date of Patent: Mar. 21, 1989

[54] BOWEL CONTROL PROBE AND METHOD FOR CONTROLLING BOWEL INCONTINENCE

[75] Inventors: Michael E. Fisher; Patricia A. Moxham, both of Reno; Brian W. Bradshaw, Sparks, all of Nev.

[73] Assignee: Healthcare Technological Resources, Inc., Sparks, Nev.

[21] Appl. No.: 22,389

[22] Filed: Mar. 6, 1987

[51] Int. Cl.$^4$ .............................................. A61B 5/00
[52] U.S. Cl. ...................................... 128/634; 128/780
[58] Field of Search ............... 128/633, 634, 664, 665, 128/780; 250/341

[56] References Cited

U.S. PATENT DOCUMENTS

| | | | |
|---|---|---|---|
| 4,197,458 | 3/1988 | Perren | 250/341 |
| 4,201,914 | 5/1980 | Perren | 250/341 |
| 4,517,984 | 5/1985 | Perlin | 128/780 X |

Primary Examiner—William E. Wayner
Attorney, Agent, or Firm—Thomas E. Schatzel

[57] ABSTRACT

A bowel control probe apparatus and method for sensing and preventing incontinent episodes. The probe comprises a catheter with an infrared (I.R.) sensor tip for sensing fecal mass in the rectum and a cuff which is inflated with air to prevent passage of the fecal mass. The method of sensing and preventing incontinent episodes includes the steps of: inserting the probe in the rectum, inflating the cuff, transmitting I.R. light into the rectum, monitoring the reflectance of I.R. light and generating an alarm signal when a predetermined amount of reflected I.R. light is measured.

24 Claims, 2 Drawing Sheets

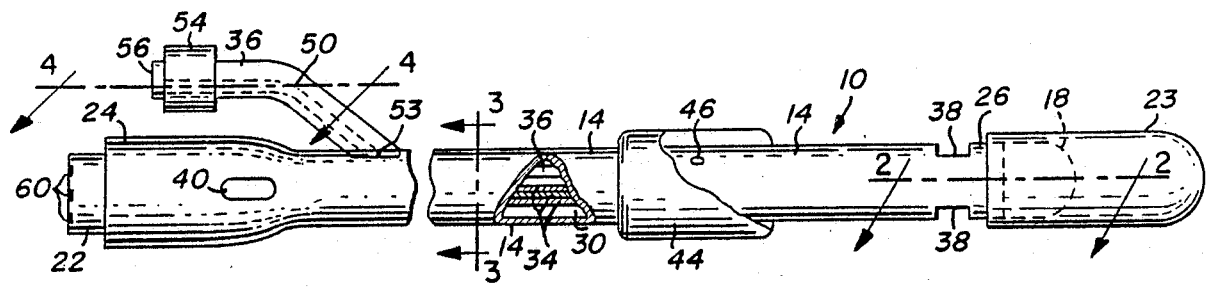
FIG_1
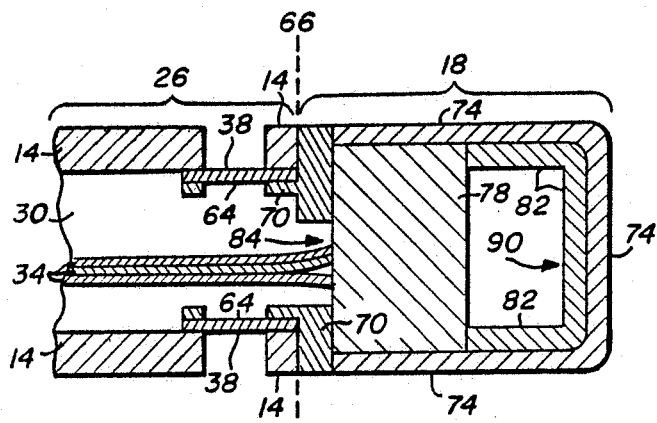
FIG_2a
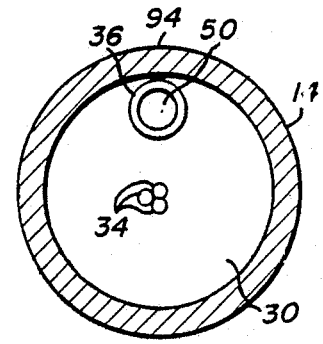
FIG_3
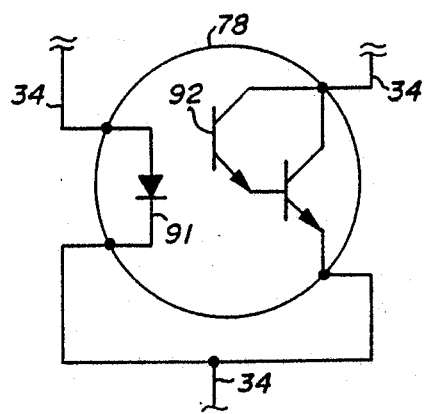
FIG_2b
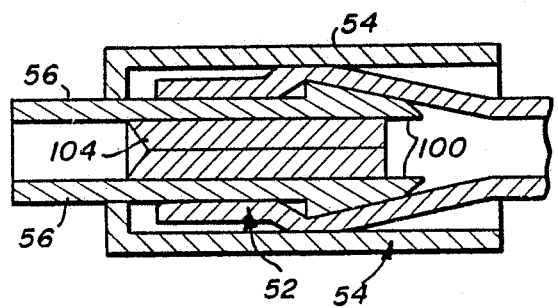
FIG_4
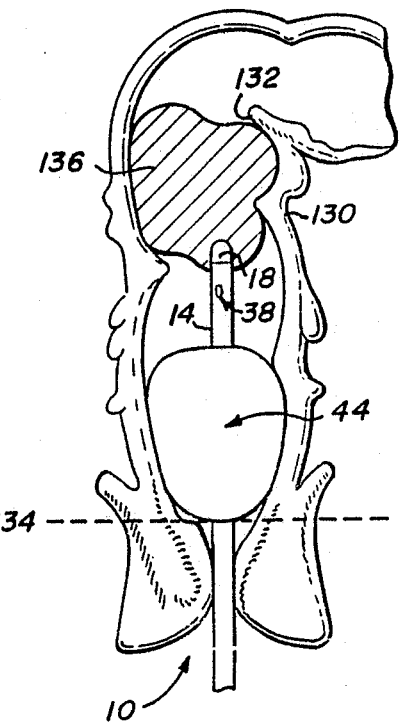
FIG_6

BOWEL CONTROL PROBE AND METHOD FOR CONTROLLING BOWEL INCONTINENCE

BACKGROUND OF THE INVENTION

1. Field of the Invention

The present invention relates generally to an apparatus and method for controlling episodes of bowel incontinence and more particularly to a probe equipped with an infrared sensor for use in detecting the presence of fecal mass in the rectum.

2. Description of the Prior Art

Many bedridden patients have little or no control over bowel movements. Besides being very embarrassing to the patient, a very unpleasant task nursing personnel endure is disposing of fecal waste after a patient's incontinent episode and cleaning the patient after such event.

Other problems associated with an incontinent episode include the excoriation of the patient's skin and risk of fecal contamination for patients and nursing personnel. Economically, the replacement of soiled bed linens, blankets and gowns compound the loss of valuable nursing time and effort.

Prior art commonly used techniques of dealing with the problem include the occasional use of rectal tubes or the use of disposable pads to protect the bed linens, the patient's skin and the like. These techniques exhibit only marginal success and do nothing to prevent bowel incontinence, but rather seek to minimize the undesirable effects of an incontinent episode. Also, U.S. Pat. No. 2,494,393 discloses a device which may be inserted and removed from the bowel outlet to dam the passage of fecal material. U.S. Pat. Nos. 4,634,443; 4,408,597; 4,587,954; 4,178,915; 3,750,194; 3,863,622; 4,386,601; 4,417,567; 4,419,985; and 4,222,377 disclose a surgically implantable device to circumscribe the bowel or urinary canal and which may be expanded and retracted to allow controlled passage of fecal material. U.S. Pat. No. 2,457,244 discloses a device to preclude premature expulsion of fluids given with an enemata and to enable a nurse to positively control rectal injections without the need for the nurse to be continuously present.

SUMMARY OF THE PRESENT INVENTION

It is therefore an object of the present invention to provide an apparatus and method for sensing the presence of fecal material in the human colon.

It is another object of the present invention to provide an apparatus and method for detection of a potential incontinent condition in a patient and to generate an alarm so that nursing personnel may be warned of the condition prior to the occurrence of the incontinent episode.

It is yet another object of the present invention to provide an apparatus and method for detecting an incontinent condition and for temporarily blocking the discharge of fecal material until such time that nursing personnel may be present.

It is a further object of the present invention to provide a method and apparatus for detection and temporarily preventing an incontinent episode which method is easy to employ and which apparatus is relatively inexpensive while, at the same time, maintaining high sanitary conditions.

Briefly, the present invention includes a probe that is inserted into the rectum of bed-ridden patients or others with dysfunctional bowel control. The probe includes an infrared (I.R.) sensor tip capable of monitoring the presence or absence of fecal mass in the rectum. When the I.R. sensor tip detects the presence of fecal mass, a signal is sent to remote monitoring equipment which alerts nursing personnel to the impending incontinent episode. The probe may also be equipped with an inflatable cuff which temporarily blocks discharge of the fecal mass until nursing personnel deflate the cuff.

An advantage is that the bowel control probe of the present invention can detect the presence of fecal mass in the rectum and provide an electrical warning signal to an attendant.

Another advantage is that the probe can temporarily restrain fecal mass discharge until nursing personnel are present.

Yet another advantage is that the probe is easy to use.

A further advantage is that the probe is relatively inexpensive.

These and other objects and advantages of the present invention will no doubt become obvious to those of ordinary skill in the art after having read the following detailed description of the preferred embodiment which is illustrated in the various drawing figures.

IN THE DRAWINGS

FIG. 1 illustrates a bowel control probe according to the present invention;

FIG. 2a is a cross-sectional view of the infrared sensor tip taken along the line 2—2 of FIG. 1;

FIG. 2b is a circuit diagram of the infrared phototransducer;

FIG. 3 is a cross-sectional view of the main catheter taken along the line 3—3 of FIG. 1;

FIG. 4 is a cross-sectional view of the air-fill port housing taken along the line 4—4 of FIG. 1;

FIG. 6 is a placement diagram for the bowel control probe of the present invention.

DETAILED DESCRIPTION OF THE PREFERRED EMBODIMENT

Figure 5:
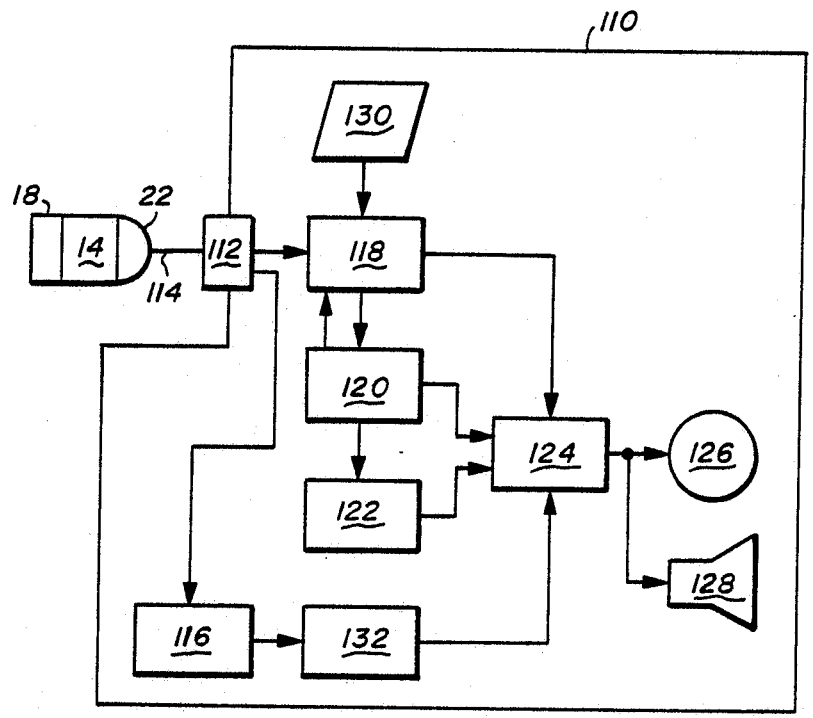
FIG. 5 is a block circuit diagram of the probe control module for use with the present invention.

Referring now to FIG. 1, there is shown a bowel control probe of the present invention referred to by the general reference numeral 10. The probe 10 comprises three basic components: a main catheter 14, a sensory tip 18 and an electrical port 22. A tip protection capsule 23 surrounds and envelops sensory tip 18. The catheter 14 is an elongated, flexible, cylindrical tube sized for insertion in the human rectum through the anus and having a proximal end 24 and a distal end 26. Inside of catheter 14 is a central lumen (or cavity) 30 extending the length of catheter 14. Contained within lumen 30 are a plurality of electrical wires 34, which extend from electrical port 22 to sensory tip 18, and an air-fill catheter 36.

A pair of gas inlet ports 38 are cut through the distal end 26 of catheter 14 and extend into underlying lumen 30. Similarly, a gas outlet port 40 is cut through the proximal end 24 of catheter 14 and into underlying lumen 30.

An inflatable torus-shaped cuff 44 circumscribes and is firmly attached to a portion of catheter 14 at a location approximately one to three centimeters from distal end 26. An inflation inlet 46 is cut through catheter 14 at a point lying underneath cuff 44. Inlet 46 opens into both cuff 44 and into an air-fill lumen 50. Air-fill lumen 50 is a cavity inside of the air-fill catheter 36. The air-fill catheter 36 is a flexible elongated tube fastened to an inside wall of catheter 14. Air-fill catheter 36 extends from inlet 46 back toward proximal end 24 but branches and exits main catheter 14 through a junction 53 at a point distal to electrical port 22. Air-fill catheter 36 terminates inside of air-fill port housing 54 (see FIG. 4). An air-fill interconnect port 56, adapted to receive the nose of an ordinary hypodermic syringe, protrudes from housing 54.

The electrical port 22 is positioned at the proximal end 24 of main catheter 14 and tightly plugs the proximal end of central lumen 30. Electrical port 22 comprises a plurality of plugs 60 to which are attached the plurality of electrical wires 34. Alternatively, plugs 60 could be a plurality of tight holes through which the plurality of electrical wires 34 pass to the outside of catheter 14.

Referring now to FIG. 2a, there is shown the sensory tip 18 and the distal end 26 of main catheter 14 in more detail (the protective capsule 23 is not shown). As can be seen there, the pair of gas inlets 38 are separated from central lumen 30 by a pair of hydrophobic gas permeable membranes 64. The sensory tip 18 interfaces with main catheter 14 along line 66. A sensor base 70 fits into lumen 30, overlapping membranes 64, and serving to attach sensory tip 18 to catheter 14. Sensory tip 18 is comprised of a the sensor base 70, a hollow cylindrical lens cap 74, which forms the outside of tip 18, and an infrared (I.R.) phototransducer 78. The plurality of electrical wires 34 pass through a hole 84, which exists in sensor base 70, and are attached to phototransducer 8. An area 82 extends along the inside surface of lens cap 74 distal to phototransducer 78. A gap 90 of open space remains between phototransducer 78 and area membrane 82. The lens cap 74 can be separated from the sensor base 70 to allow access to phototransducer 78. FIG. 2b shows that phototransducer 78 is a simple semiconductor circuit comprising an infrared emitting diode 91 and a phototransistor 92.

FIG. 3 is a cross-sectional view of main catheter 14 showing the proper orientation of the plurality of electrical wires 34 to central lumen 30, air-fill catheter 36 and air-fill lumen 50. It can also be seen from this orientation that air-fill catheter 36 is attached to the inside surface of main catheter 14 along a site 94.

FIG. 4 shows a more detailed diagram of the air-fill port housing 54. As can be seen, the air-fill interconnect port 56 has a pair of flanged tips 100 which fit inside of air-fill catheter 52. An air check valve 104 fits between flanged tips 100. Valve 104 allows air to be injected into air-fill lumen 50, and thus into the cuff 44 of FIG. 1, but automatically closes to prevent loss of pressure.

FIG. 5 shows a block diagram of a probe control module 110. The electrical port 22 is connected to a jack 112 by a connector 114. Jack 112 is connected to a rechargeable power supply 116 and to a trigger amplifier 118. The amplifier 118 is connected to a jack connect logic circuit 120 which is connected to an eight hour clock 122 and an alarm coder driver 124. The alarm coder driver 124 activates an optical alarm indicator 126 and an audio alarm 128. The sensitivity of trigger amplifier 118 can be adjusted with a sensitivity adjust circuit 130 to prevent spurious triggering of alarms 126 and 128. A low charge detector 132 is connected between the rechargeable power supply 116 and alarm coder driver 124 to activate alarms 126 and 128 when recharging of power supply 116 is required.

FIG. 6 shows the placement of the bowel control probe 10 of the present invention inserted in a human rectum 130. Location 132 represents the rectosigmoid junction in the human colon and line 134 is the anorectal line. When a fecal mass 136 is present within the proximity of sensory tip 18, an electrical signal is generated in the I.R. phototransducer 78. This signal is transmitted through electrical wires 34 and connector 114 to the control module 110 where the alarms 126 and 128 are activated indicating an eminent incontinent episode.

The functioning of the sensory tip 18, shown in FIG. 2a, can now be more thoroughly described. A low voltage current is transmitted from the control module 110 to the I.R. phototransducer 78 through one of the electrical wires 34. This causes I.R. light to be transmitted across gap 90. When fecal mass 132 is not present within proximity of sensory tip 18, I.R. light passes through area 82 and is emitted from tip 18. When fecal mass 132 is present within proximity of tip 18, I.R. light is reflected and/or scattered off fecal mass 132 and back into area 82 where it is collected at phototransducer 78. Collection of I.R. light at phototransducer 78 generates an electrical impulse which is transmitted back to control module 110 by the electrical wires 34 and connector 114. The electrical impulse can then be utilized to activate the alarms 126 and 128 warning of an impending episode of bowel incontinence. A background amount of reflected I.R. light may be measured and disregarded using sensitivity adjust circuit 130 so as to eliminate spurious alarms.

The inflatable cuff 44 functions as a physical block in the colon, adjacent the anus, to prevent passage of the fecal mass 132 until an appropriate time. The cuff 44 is inflated, after insertion of the probe 10 in the rectum, by pumping air from a syringe inserted in air-fill interconnect port 56 to cuff 44 via the air-fill catheter 36. Similarly, when voiding of the rectum 130 is desired, cuff 44 can be deflated by releasing pressure through port 56.

The gas inlet ports 38 function to relieve flatus that may build up in rectum 130 when cuff 44 is inflated. Gas from rectum 130 passes through ports 38 and membranes 64 into central lumen 30. It is then vented distally to cuff 44 through gas outlet port 40.

The tip protection capsule 23 is fitted over sensor tip 18 to protect tip 18 from contamination by residual fecal matter during insertion of the bowel control probe 10 in rectum 130. Capsule 23 is designed to dissolve at body temperature (e.g., about 98.5° C.) approximately 10-20 seconds after insertion in rectum 130.

In the preferred embodiment of the present invention, cuff 44 may be similar in construction and material to a high volume-low pressure endotracheal cuff. Main catheter 14 and air-fill catheter 36 may be any suitable, flexible medical tubing and cuff 44 can be attached to catheter 14 with a suitable adhesive or by ultrasonic welding. The infrared phototransducer 78 may be obtained from numerous commercial sources. For example, Honeywell Plastic Reflective Assembly No. HLC 1395-001 or a TRW Reflective Object Sensor No. OPB710F will function satisfactorily. The power supply 116 can be either a rechargeable nickel cadmium battery pack or 115-volt external power supply. The tip protection capsule 23 can be a gelatin capsule.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. A bowel control probe for detecting the presence of fecal material in the human rectum comprising:
   a flexible main catheter sized for insertion into the rectum through the anus and having a central lumen which serves as a housing for a plurality of electrical wires;
   an infrared sensing means for detecting the presence of fecal mass in the rectum attached near a distal end of the main catheter and to said electrical wires;
   a lens cap which substantially surrounds the infrared sensing means and which is substantially transparent to infrared light; and
   an electrical port located near a proximal end of the main catheter which provides access to said plurality of electrical wires.

2. The apparatus of claim 1 wherein, the infrared sensing means is a device which transmits and receives infrared radiation.

3. The apparatus of claim 1 wherein, the electrical port comprises a plug which allows the plurality of electrical wires to be connected to equipment external to the main catheter.

4. The apparatus of claim 1 further comprising:
   at least one piece of auxiliary equipment connected to said plurality of electrical wires through the electrical port and functioning to supply power to the infrared sensing means and to receive signals from the infrared sensing means through said plurality of electrical wires.

5. The apparatus of claim 4 wherein, one piece of the auxiliary equipment comprises a rechargeable battery pack.

6. The apparatus of claim 4 wherein, one piece of the auxiliary equipment comprises an alarm which indicates the presence of fecal mass in response to a signal from the infrared sensing means.

7. The apparatus of claim 1 further including:
   an inflatable cuff located between the sensing means and the electrical port for preventing the passage of fecal material therearound;
   an inflation means for inflating the inflatable cuff; and
   a pressure release means for relieving flatus.

8. The apparatus of claim 7 wherein, the inflation means comprises a second catheter located inside the main catheter, and having one end of the second catheter opening into the inflatable cuff and the other end of the second catheter exiting the main catheter near said proximal end of the main catheter and terminating in a pressure port.

9. The apparatus of claim 7 wherein the pressure release means comprises:
   one or more gas inlet openings located in the distal end of the main catheter leading into the said central lumen;
   one or more gas-permeable membranes positioned between each gas inlet opening and the said central lumen; and
   at least one gas outlet openings located in said proximal end of the main catheter and opening into said central lumen.

10. The apparatus of claim 1 further comprising:
    a means for protecting the infrared sensing means from fecal contamination during insertion of the bowel control probe in the rectum.

11. The apparatus of claim 10 wherein, the means for protecting the infrared sensing means from fecal contamination is a gelatin capsule which dissolves at body temperature.

12. A method for detecting impending episodes of bowel incontinence which comprises:
    a. inserting an I.R. sensor into the rectum of a patient;
    b. transmitting I.R. light from the I.R. sensor into the rectum;
    c. monitoring the reflectance and scattering of I.R. light off a fecal mass; and
    d. generating an alarm signal when a predetermined amount of reflected I.R. light is measured indicating the presence of said fecal mass.

13. A method for controlling episodes of bowel incontinence which comprises:
    a. inserting a catheter having an I.R. sensor and an inflatable cuff into the rectum of a patient;
    b. inflating the inflatable cuff so as to block discharge from the rectum;
    c. transmitting I.R. light from the I.R. sensor into the rectum;
    d. monitoring the reflectance and scattering of I.R. light off a fecal mass; and
    e. generating an alarm signal when a predetermined amount of reflected I.R. light is measured indicating the presence of said fecal mass; and
    f. deflating the inflatable cuff under controlled circumstances in response to the generated alarm signal.

14. A bowel control probe for detecting the presence of fecal material in the human rectum comprising:
    a main catheter sized for insertion into the rectum through the anus and having an central lumen which serves as a housing for a plurality of electrical wires;
    an infrared sensing means for detecting the presence of fecal mass in the rectum attached near a distal end of the main catheter and to said electrical wires;
    an electrical port located near a proximal end of the main catheter which provides access to said plurality of electrical wires;
    an inflatable cuff located between the sensing means and the electrical port for preventing the passage of fecal material therearound; and
    an inflation means for inflating the inflatable cuff.

15. The apparatus of claim 14 wherein, the inflation means comprises a second catheter located inside the main catheter, and having one end of the second catheter opening into the inflatable cuff and the other end of the second catheter exiting the main catheter near said proximal end of the main catheter and terminating in a pressure port.

16. The apparatus of claim 14 wherein, the electrical port comprises a plug which allows said plurality of electrical wires to be connected to equipment external to the main catheter.

17. The apparatus of claim 14 wherein the infrared sensing means comprises:
    an infrared light emitting diode; and
    a phototransistor.

18. The apparatus of claim 14 further comprising:
    a pressure release means for relieving flatus.

19. The apparatus of claim 14 further comprising:

at least one piece of auxiliary equipment connected to said plurality of electrical wires through the electrical port and functioning to supply power to the infrared sensing means and to receive signals from the infrared sensing means through said plurality of electrical wires.

20. The apparatus of claim 14 further comprising:
a means for protecting the infrared sensing means from fecal contamination during insertion of the bowel control probe in the rectum.

21. The apparatus of claim 20 wherein,
the means for protecting the infrared sensing means from fecal contamination is a gelatin capsule which dissolves at approximately normal body temperature.

22. The apparatus of claim 18 wherein the pressure release means comprises:

at least one gas inlet opening located in said distal end of the main catheter opening into said central lumen;
at least one gas-permeable membrane positioned between each gas inlet opening and said central lumen; and
at least one gas outlet opening located in said proximal end of the main catheter and opening into said central lumen.

23. The apparatus of claim 19 wherein,
one piece of the auxiliary equipment comprises a rechargeable battery pack.

24. The apparatus of claim 19 wherein,
one piece of the auxiliary equipment comprises an alarm which indicates the presence of fecal mass in response to a signal from the infrared sensing means.

* * * * *